United States Patent [19]

Pless et al.

[11] Patent Number: 5,007,422
[45] Date of Patent: Apr. 16, 1991

[54] METHOD FOR COMBINER CARDIAC PACING AND DEFIBRILLATION

[75] Inventors: Benjamin Pless; Michael Sweeney, both of Menlo Park; Roger Winkle, Palo Alto, all of Calif.; Anthony Nathan, Bushey Heath, England

[73] Assignee: Ventritex, Inc., Sunnyvale, Calif.

[21] Appl. No.: 362,163

[22] Filed: Jun. 6, 1989

[51] Int. Cl.⁵ .................................... A61N 1/362
[52] U.S. Cl. ........................ 28/419 PG; 128/419 D
[58] Field of Search ................... 128/419 D, 419 PG

[56] References Cited

U.S. PATENT DOCUMENTS

| | | | |
|---|---|---|---|
| 4,407,288 | 10/1983 | Langer et al. | 128/419 PG |
| 4,475,551 | 10/1984 | Langer et al. | 128/419 D |
| 4,485,818 | 12/1984 | Leckrone et al. | 128/419 PG |
| 4,548,209 | 10/1985 | Wielders et al. | 128/419 D |
| 4,559,946 | 12/1985 | Mower | 128/419 PG |
| 4,787,389 | 11/1988 | Tarjan | 128/419 D |
| 4,819,643 | 4/1989 | Menken | 128/419 D |

Primary Examiner—William E. Kamm
Assistant Examiner—Scott M. Getzon
Attorney, Agent, or Firm—Gerstman & Ellis, Ltd.

[57] ABSTRACT

A method is disclosed for combined cardiac pacing and defibrillating with an implanted pacer/defibrillator having sensing and pacing leads connected to the atrium and the ventricle. P-waves and R-waves are sensed, and V—V timer and a V—A timer are reset if an R-wave is sensed. If an R-wave is sensed during the V—V timer interval, a pacing stimulus to the ventricle is inhibited. If a P-wave is sensed during the V—A timer interval, a pacing stimulus to the atrium is inhibited. In an R-wave is sensed during the V—V timer interval, arrhythmia therapy is provided if an arrhythmia is determined to be present. If the sensed ventricular rate is greater than a selected tachycardia rate but is less than a selected fibrillation rate, then a determination is made whether the sensed atrial rate is greater than a selected fibrillation rate, and if so, the V—V and V—A timers are reset, but if the sensed atrial rate is not greater than a selected fibrillation rate, then arrhythmia therapy is provided. If an arrhythmia is present, the charging of a capacitor commences but if the arrhythmia ceases, the charging discontinues. If the capacitor is charged and the arrhythmia is still present, then a shock is delivered to the heart during a time period that is outside the vulnerable zones of the atrium and the ventricle.

23 Claims, 5 Drawing Sheets

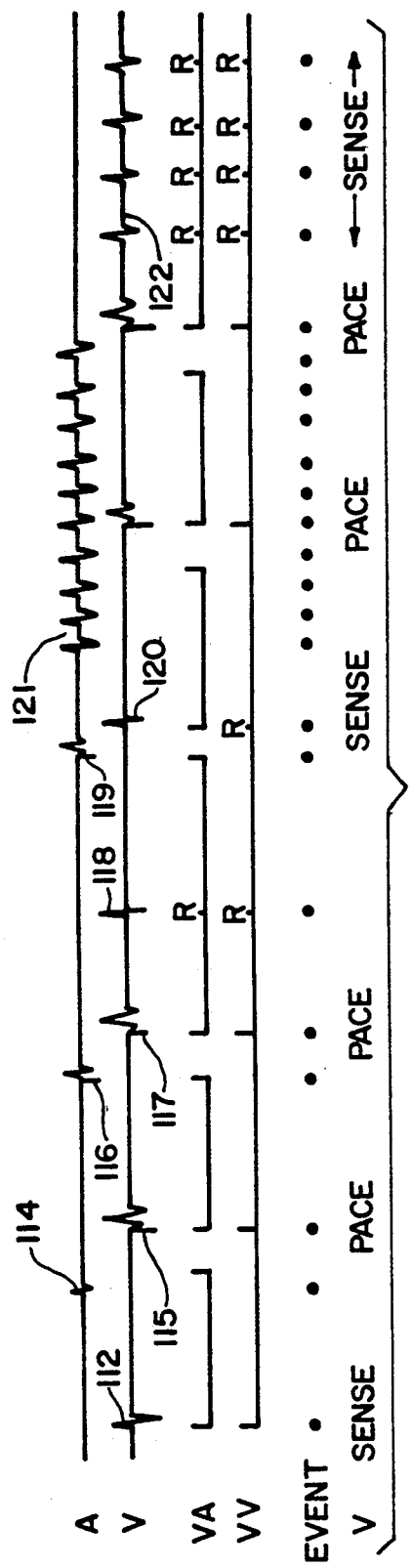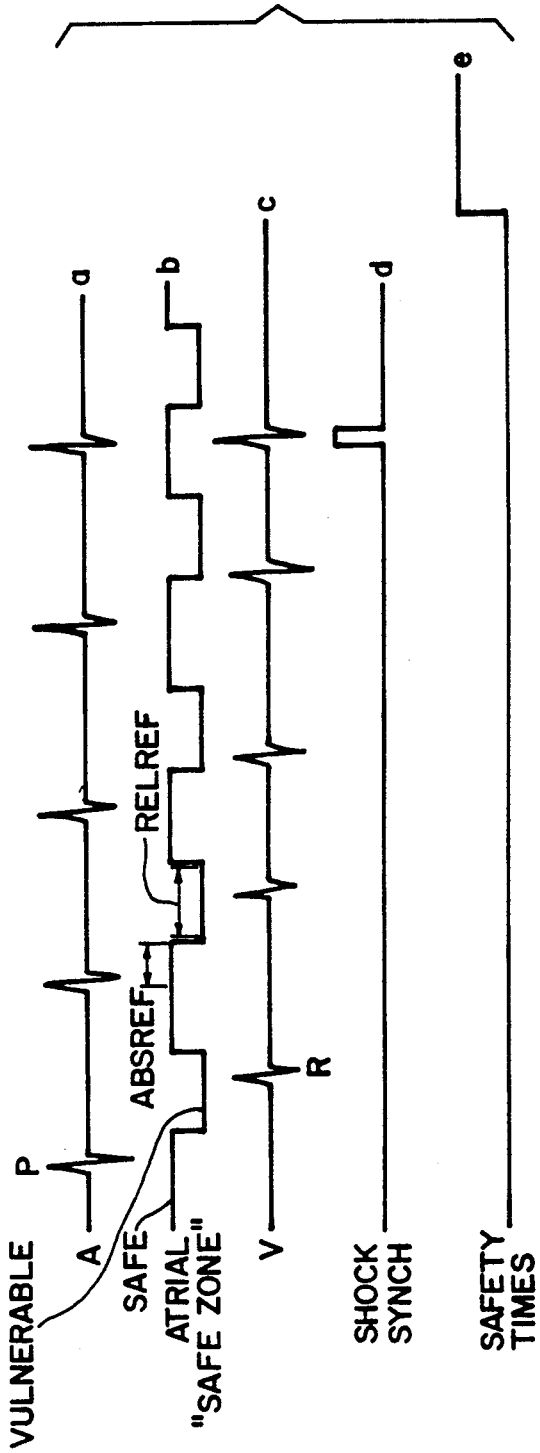

METHOD FOR COMBINER CARDIAC PACING AND DEFIBRILLATION

FIELD OF THE INVENTION

The present invention concerns a novel system for pacing and defibrillating using an implanted pacer/defibrillator.

BACKGROUND OF THE INVENTION

Prior art systems are known in which a pacer and defibrillator are combined in a single unit for pacing the heart and for defibrillating the heart when required. Pacers provide, to the heart, relatively low energy pacing pulses while defibrillators, also known as cardioverters, provide far greater energy. An example of an implantable cardiac/defibrillator is found in Rubin U.S Pat. No. 3,857,398.

We have found that it is desirable to provide dual chamber bradycardia support to defibrillator patients. We have also discovered a method for preventing the incidence of atrial fibrillation caused by ventricular defibrillation shocks.

In prior art implantable defibrillators, none are known with dual chamber pacing and defibrillation modalities. Further, prior art defibrillators are typically synchronous to the ventricle.

We have found that a defibrillator that has dual chamber pacing capability can be provided, with the preferred mode being a DDI[1] pacer. Although DDD pacing is typically chosen by cardiologists when available, we have found that DDD pacing is inappropriate for defibrillators. That is because the ability to track the ventricular pacing rate in the presence of an atrial arrhythmia can be arrhythmogenic. Further, DVI pacing is asynchronous in the atrium, and is likely to be arrhythmogenic in those patients in whom a propensity for arrhythmias is known. In contrast, DDI pacing neither tracks nor is asynchronous and therefore we consider DDI pacing to be the preferred mode.

[1] The symbols DDI, DDD, DVI, etc. are used herein in accordance with the Intersociety Commission on Heart Diseases Resources code.

We have also found that with a sensing electrode in the atrium as well as in the ventricle, it is possible to synchronize the shock to either chamber. Generally if there is a fast ventricular tachycardia or fibrillation, the synchrony with the ventricle is unimportant and it is better to synchronize to the atrium to avoid inducing atrial fibrillation. However, for a slow ventricular tachycardia, it may still be desirable to synchronize with the ventricle in order to avoid inducing ventricular fibrillation. In this case it may still be possible to synchronize with the "safe zone" of the atrial cycle, that is, within either approximately 80 msec. of the P-wave or 230 msec. after it.

It is, therefore, an object of the present invention to provide dual chamber bradycardia support for patients with the need for implantable defibrillation, with the minimum of adverse device mode interaction.

Another object of the present invention is to reduce the incidence of atrial fibrillation induced by shocks for ventricular tachyarrhythmias.

Other objects and advantages of the present invention will become apparent as the description proceeds.

SUMMARY OF THE INvENTION

In accordance with the present invention, a method is provided for combined cardiac pacing and defibrillating with an implanted pacer/defibrillator having sensing and pacing leads connected to the atrium and the ventricle. The method comprises the steps of: sensing for P-waves; sensing for R-waves; resetting a V—V timer and a V-A timer if an R-wave is sensed; providing a pacing stimulus to the ventricle if no R-wave is sensed during the V—V timer intervals; inhibiting the pacing stimulus to the ventricle if an R-wave is sensed during the V—V timer interval; inhibiting a pacing stimulus to the atrium if a P-wave is sensed during the V-A timer interval; if an R-wave is sensed during the V—V timer interval, then determining the presence of an arrhythmia; and providing arrhythmia therapy if an arrhythmia is determined to be present.

As used herein in the specification and claims, the terms (a) "V—V timer" and (b) "V-A timer" include any timing means such as a single timer or a series of timers or a combination of timers for timing, respectively, (a) a ventricular to atrial time interval. For example, a V—V timer could include a refractory timer plus a noise timer plus an alert interval timer, etc.

In the illustrative embodiment, any shock delivered to the heart is delivered during a time period that is outside the vulnerable zones of the atrium and ventricle.

In accordance with the method of the present invention, if no arrhythmia is determined to be present, then the V—V and V-A timers are reset. If no R-wave or P-wave is sensed during the V-A timer interval, then a pacing stimulus is provided to the atrium only if an R-wave wave was sensed during the previous V—V timer interval.

A more detailed explanation of the invention is provided in the following description and claims, and as illustrated in the accompanying drawings.

BRIEF DESCRIPTION OF THE DRAWINGS

FIG. 5 is a timing diagram of DDI pacing in accordance with the principles of the present invention.

FIG. 6 is another timing diagram illustrating the synchronization of ventricular shock with an atrial "safe zone" in accordance with the principles of the present invention.

DETAILED DESCRIPTION OF THE ILLUSTRATIVE EMBODIMENT

Figure 1:
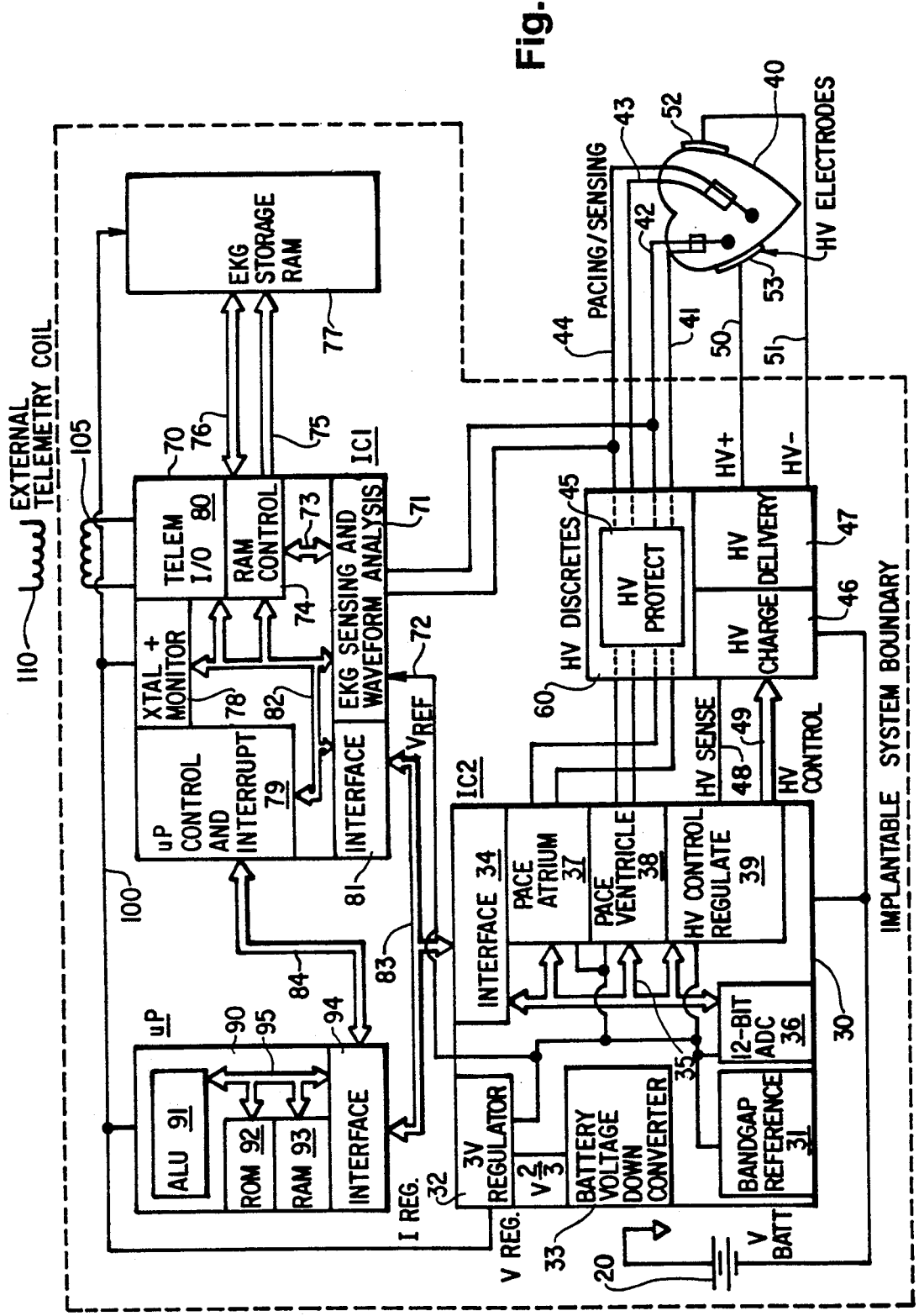
FIG. 1 is a block diagram of an implantable pacer/defibrillator constructed in accordance with the principles of the present invention.

Referring to FIG. 1, the block diagram for the implantable defibrillator includes four ICs and a set of high voltage discretes. The battery produces a positive voltage with respect to ground that varies from about 6.4 volts when new, to 5.0 volts at the end of service. The battery directly powers IC2 30 and the high voltage discretes 60.

IC2 contains a band-gap reference circuit 31 that produces 1.235 volts, and 3 volt regulator that powers the microprocessor 90, IC1 70, and the ECG storage RAM 77 through line 100. The 3 volt regulator runs off of a switched capacitor V ⅔ battery voltage down converter 33 for improved efficiency.

The microprocessor 90 communicates with IC2 through a data and address bus 83 and an on-chip interface 34 that contains chip-select, address decoding and data bus logic as is typically used with microprocessor peripherals. The internal bus 35 allows the microprocessor to control a general purpose ADC 36, the atrial pace circuits 37, the ventricular pace circuits 38, and the HV control and regulate block 39.

The ADC 36 is used by the microprocessor to measure the battery and other diagnostic voltages within the device.

The atrial pace circuits 37 include a DAC that provides the ability to pace at regulated voltages. It communicates with the atrium of a heart 40 through two lines. One line 41 is a switchable ground; the other line 42 is the pacing cathode and is also the input to the atrial sense amplifier, as will be described below.

The ventricular pace circuits 37 include a DAC that provides the ability to pace at regulated voltages. It communicates with the ventrical of a heart 40 through two lines. One line 43 is a switchable ground; the other line 44 is the pacing cathode and is also the input to the ventricular sense amplifier, as will be described below.

Both the atrial and ventricular pace lines pass through high voltage protection circuits 45 to keep the defibrillation voltages generated by the device from damaging the pacing circuits 37 and 38.

The HV control and regulate block 39 on IC2 30 is used by the microprocessor 90 to charge a high voltage capacitor included in the HV charge block 46 to a regulated voltage, and then to deliver the defibrillating pulse to the heart 40 through the action of switches in the HV delivery block 47. An HV sense line 48 is used by the HV regulation circuits 39 to monitor the defibrillating voltage during charging. An HV control bus 49 is used by the HV control circuits 39 to control the switches in the HV delivery block 47 for delivering the defibrillating pulse to the electrodes 52, 53 through lines 50 and 51.

IC1 70 is another microprocessor peripheral and provides timing, interrupt, telemetry, ECG storage, and sensing functions.

A dual channel electrogram sensing and waveform analysis section 71 interfaces with the atrium and ventricle of the heart 40 through lines 42 and 44 respectively. The sensed electrogram is amplified and digitized. The amplifiers contained in this section 71 have multiple gain settings that are under microprocessor control for maintaining an AGC. Features such as peak voltage and complex width are extracted by the waveform analysis circuits 71 for the microprocessor 90 to use in discriminating arrhythmias from normal sinus rhythm. The voltage reference 31 from IC2 30 is used by the digitizer circuit 71 in the usual fashion, and is supplied by line 72.

The digitized ECG is provided to the RAM controller 74 through a bus 73. The RAM controller sequences through the addresses of a static RAM 77 to maintain a pretrigger area, and this produces a post trigger area upon command from the microprocessor 90.

The crystal and monitor block 78 has a 100KHz crystal oscillator that provides clocks to the entire system. The monitor is a conventional R-C oscillator that provides a back-up clock if the crystal should fail.

The microprocessor communicates with IC1 through two buses, 83 and 84. One bus 83 is a conventional data and address bus and goes to an on-chip interface 81 that contains chip select, address decoding and data bus drivers as are typically used with microprocessor peripherals. The other bus 84 is a control bus. It allows the microprocessor to set up a variety of maskable interrupts for events like timer timeouts, and sense events. If an interrupt is not masked, and the corresponding event occurs, an interrupt is sent from IC1 70 to the microprocessor 90 to alert it of the occurrence. On IC1 70, the up control and interrupt section 79 contains microprocessor controllable timers and interrupt logic.

The device can communicate with the outside world through a telemetry interface 80. A coil 105 is used in a conventional fashion to transmit and receive pulsed signals. The telemetry circuits 80 decode an incoming bit stream from an external coil 110 and hold the data for subsequent retrieval by the microprocessor 90. When used for transmitting, the circuit 80 receives data from the microprocessor 90, encodes it, and provides the timing to pulse the coil 105. The communication function is used to retrieve data from the implanted device, and to change the modality of operation if required.

The microprocessor 90 is of conventional architecture comprising an ALU 91, a ROM 92, a RAM 93, and interface circuits 94. The ROM 92 contains the program code that determines the operation of the device. The RAM 93 is used to modify the operating characteristics of the device as regards modality, pulse widths, pulse amplitudes, and so forth. Diagnostic data is also stored in the RAM for subsequent transmission to the outside world. The Algorithmic Logic Unit (ALU) 91 performs the logical operations directed by the program code in the ROM.

The program code is written to perform certain desirable functions which are best described in flow chart form.

Referring to the timing diagram of FIG. 5, the top waveform shows atrial activity, the next waveform shows ventricular activity, the next line is the V-A timer, the next line is the V—V timer, the next line is the event position, the next line is the designation of the ventricular event, and the bottom line is the designation of the atrial event.

The first event 112 is a ventricular sense event. Whenever a ventricular event is either sensed or paced, the V-A and V—V timers start. In this instance, there is an atrial event 114 before the end of the V-A time out, signifying no atrial pacing event is required. However, the V—V timer timed out when the ventricle was paced 115. At that time, the V—V and V-A timers start again. Then the V-A timer timed out without any interposed spontaneous atrial activity so the atrium was paced 116. The V—V timer also timed out so the ventricle was paced 117. Then there was a premature ventricular contraction (PVC) 118 that constitutes a ventricular event with no preceding atrial event, which occurred within the V-A time period. This reset both the V-A and the V—V timers. Then the V-A timer timed out resulting in a paced event in the atrium 119 but there was a spontaneous ventricular event 120 before the V—V timer timed out. That reset the V—V timer and the V-A timer. At this time there was a high atrial rate commenced 121 and it is seen that even though the high atrial rate occurred, unlike the DDD pacemaker the ventricle does not track and is maintained at the V—V underlying rate. Then, thereafter there is a high ventricular rate 122 in which the R-waves are occurring more rapidly than the V-A timer time out, and this results in no atrial support. The atrium is essentially asystolic and the ventricle has a high rate.

If a DDD pacemaker were being used, and a high atrial rate occurred, a high ventricular rate would result. That undesirable result does not occur with the DDI pacer.

If the pacemaker were in a DVI mode, at the first event where an atrial time out occurred before the V-A timer timed out, a pacing pulse would have occurred in the vulnerable zone of the P-wave which could have been arrhythmogenic. However, in the instant case the DDI mode performed properly because it did not pace in the vulnerable zone of the P-wave.

Figure 2:
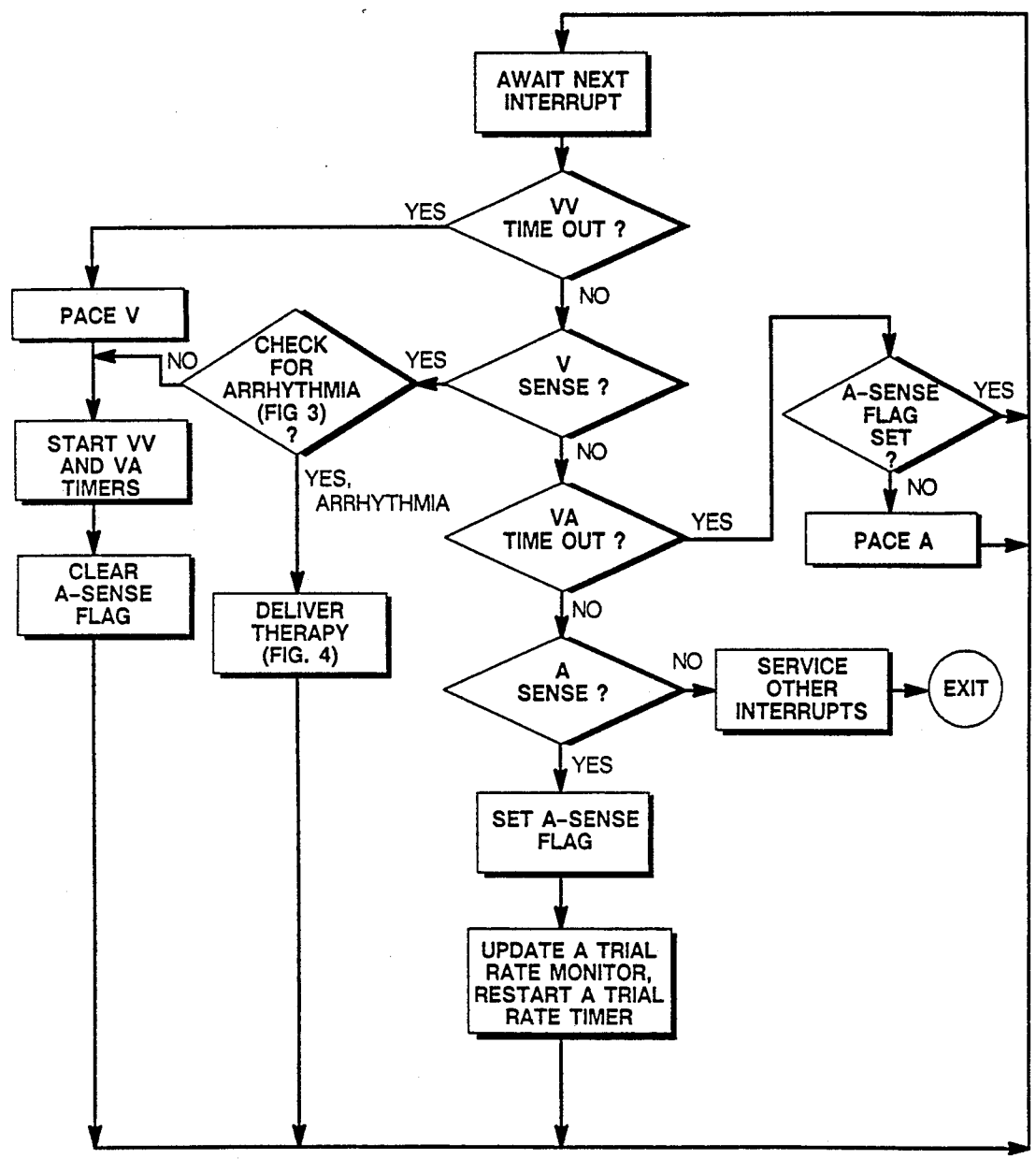
FIG. 2 is a DDI pacing/defibrillator flow chart showing the operation in accordance with the principles of the present invention.
Figure 3:
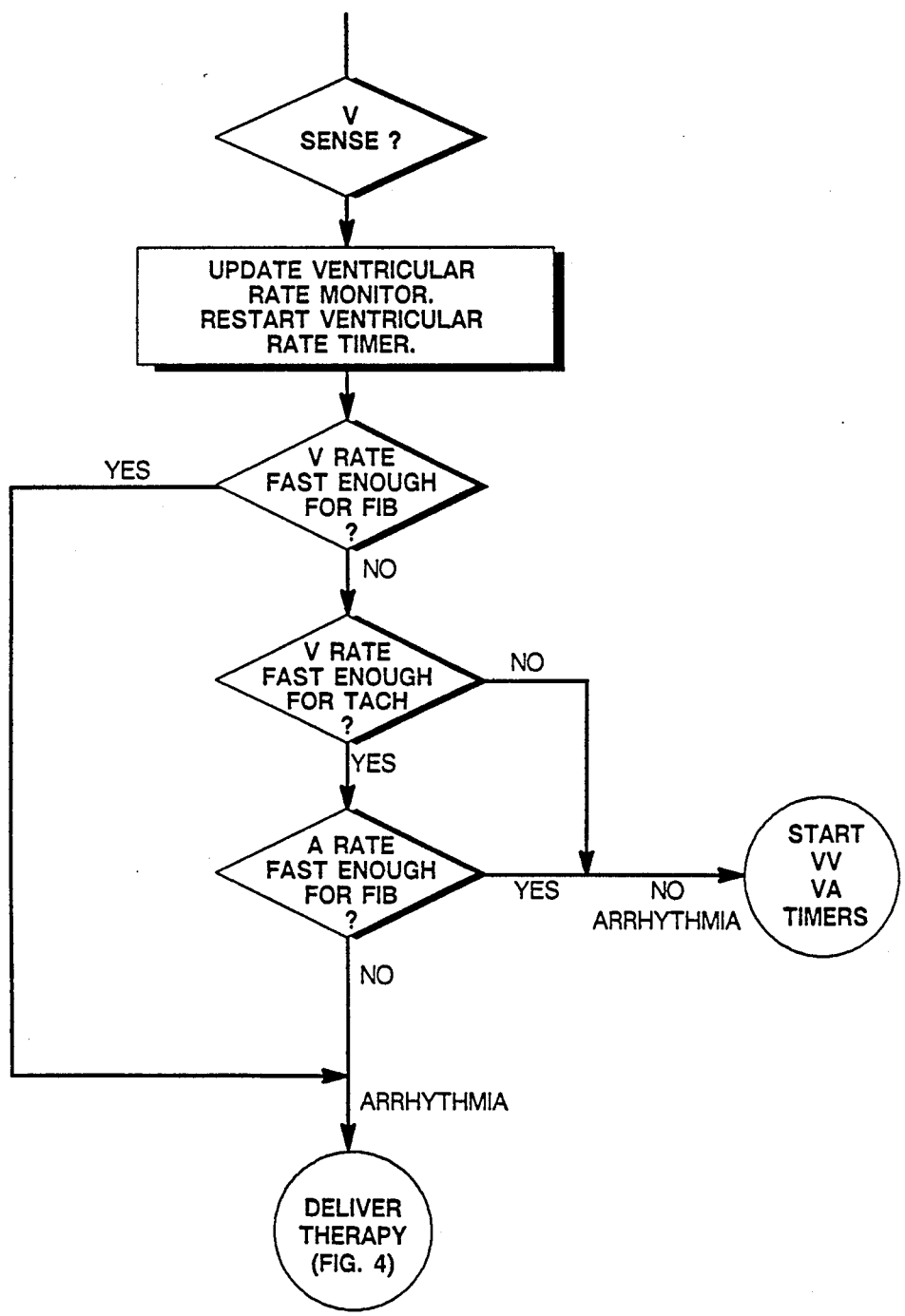
FIG. 3 is a flow chart of the "check for arrhythmia" decision block of FIG. 2, showing the operation according to the principles of the present invention.
Figure 4:
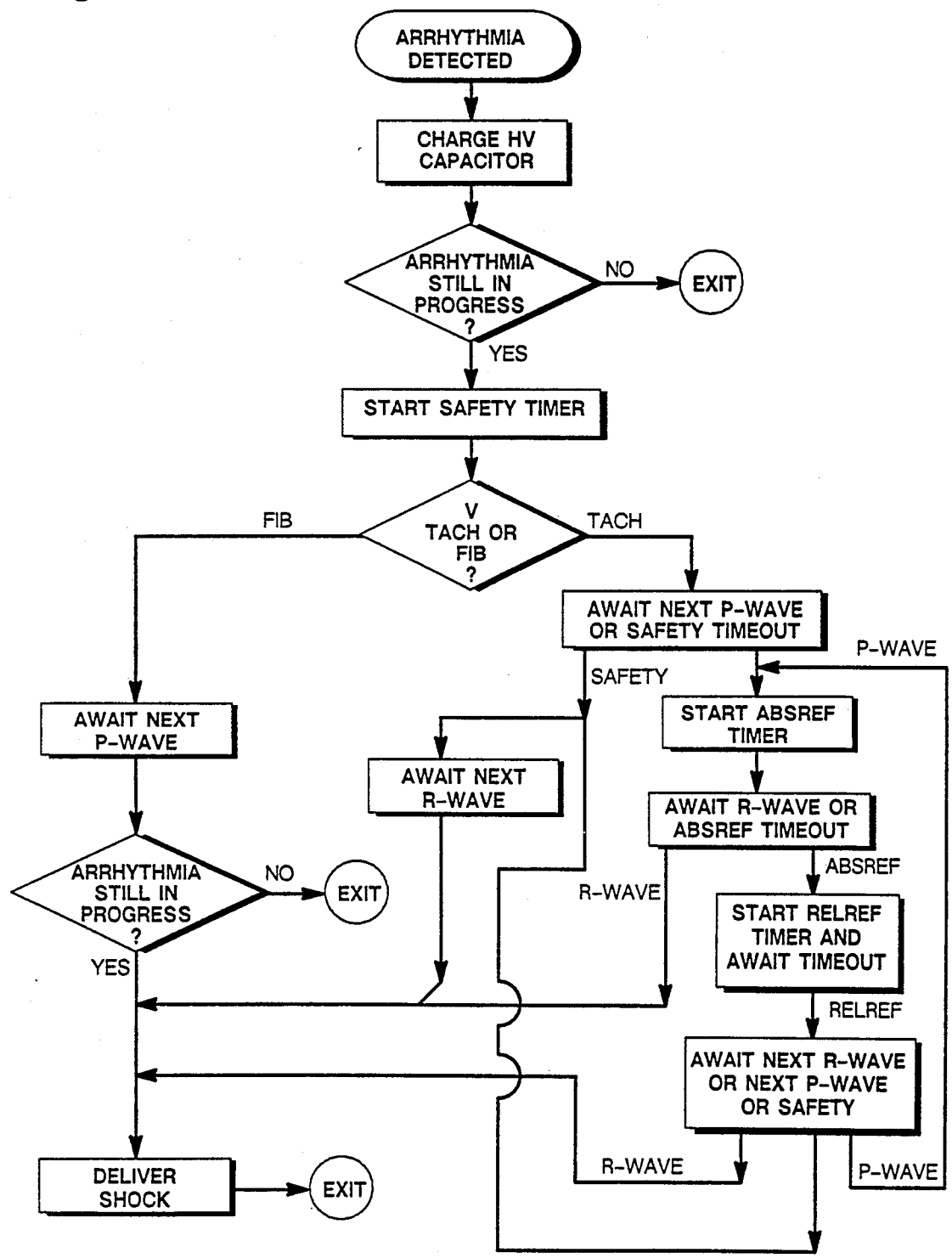
FIG. 4 is a flow chart of the "deliver therapy" decision block of FIG. 2 showing a method of operation in accordance with the principles of the present invention.

The operation of the combined DDI pacer and defibrillator is set forth in FIGS. 2, 3 and 4, which comprise flow charts of the operation of the system of FIG. 1. Referring to the flow chart of FIG. 2, the microprocessor that controls the system operates in a loop which returns to the top of the loop to a block called "await next interrupt". The microprocessor can be interrupted, meaning that its clock is restarted by a number of occurrences. If the V—V timer times out, then the ventricle is paced. After the ventricle is paced, the V—V timer and the V-A timer are started over again. The atrial sense flag is cleared and the system loops back to await the next interrupt.

In other words if the V—V timer had not timed out and an R-wave was sensed, there is a check for arrhythmia which can either result in therapy, or, if it does not result in therapy, it will return back to the same place that the pace event occurred. However, instead of pacing, the V—V timer and the V-A timer are started and the atrial sense flag is cleared. A loop back to the await next interrupt then occurs.

If there was no V—V timer time out and also if there was no ventricular sensed event, then a determination is made whether the V-A timer timed out. If the V-A timer timed out, a system determines if an atrial flag was set. If so, that means there was not a spontaneous P-wave during the V-A timer period and therefore the atrium is paced. If the atrial sense flag was set, it means that there was a P-wave sensed during the previous V-A timer period. In that case, the atrium is not paced and the system returns to the next interrupt.

If the system falls through the first three decision blocks (V—V time out, V-sense, and V-A time out) and the signal in the atrium is sensed, then the atrial sense flag is set, the atrial rate monitor is updated and the atrial rate timer is restarted. The atrial rate timer times the interval between P-waves and the atrial rate monitor provides an average of those. The system then returns to the next interrupt.

If the system falls through all four decision blocks (V—V time out, V-sense, V-A time out and A-sense), then either the microprocessor was set up to service another interrupt or there is an error. For example, another interrupt may be from the telemetry section, indicating that the programmer wishes to down-load new program parameter settings. In that case the exit would go to service the telemetry.

The check for arrhythmia block is shown in flow chart form in FIG. 3. Referring to FIG. 3, this block is entered every time an R-wave is sensed. When an R-wave is sensed, the ventricular rate monitor is updated. The ventricular rate monitor is a short term average of the R—R intervals. The ventricular rate timer is restarted for the next time sensed. If the ventricular rate is fast enough for fibrillation, the system falls through immediately to the deliver therapy block. If the ventricular rate is not fast enough for fibrillation, the system checks to see if the ventricular rate is fast enough for tachycardia. If it is not fast enough for tachycardia, the system determines if there is no arrhythmia.

If the ventricular rate is fast enough for tachycardia, the system checks the atrial rate. If the atrial rate is slow, this indicates that there is no atrial fibrillation. The system falls through and determines that there is a ventricular arrhythmia, in other words there is a fast ventricular rate, but there is an atrial rate that is not fast enough for atrial fibrillation. In that case therapy is delivered.

If the ventricular rate is fast enough for tachycardia, and the atrial rate is fast enough for fibrillation, then therapy is not delivered and the system falls through to the "no arrhythmia". The reason for this is that if the patient has an atrial rate that is higher than his ventricular rate, the system determines that the arrhythmia is an atrial based arrhythmia. In that case, the system does not provide ventricular therapy.

The deliver therapy block is illustrated in the flow chart of FIG. 4. When an arrhythmia is detected, the system falls through to the deliver therapy flow chart (FIG. 4). The therapy delivered will be cardioversion or defibrillation. Therefore, when an arrhythmia is detected, the high voltage capacitors begin charging. If the arrhythmia was tachycardia, the capacitors would be charged to a cardioversion voltage. If the arrhythmia was fibrillation, the capacitors would be charged to a defibrillation voltage. The system checks to determine if an arrhythmia is still in progress. If an arrhythmia is not still in progress, it exits. If the arrhythmia is still in progress, the system enters the synchronization block. The remaining portion of the flow chart of FIG. 4 concerns the synchronization of the shock.

First, a safety timer is started. In the illustrative embodiment, the safety timer is a timer that runs for approximately five seconds. During this time, if the system has been unable to synchronize the shock in the desired manner, the system proceeds to synchronize to the next R-wave and delivers the shock.

A determination is made whether the patient has ventricular tachycardia or fibrillation. If the patient has fibrillation, which could also be a very high rate tachycardia, the system awaits the next P-wave, verifies that the arrhythmia is still in progress, and delivers the high voltage shock to the heart. The system does not attempt to synchronize with the ventricle; it synchronizes with the atrium thereby avoiding an atrial arrhythmia.

If the system determines that a lower rate tachycardia is in progress, then the system will try to synchronize to the R-wave during the safe period of the atrial cycle. The safe period of the atrial cycle is defined as being outside of the vulnerable zone of the atrium.

First, the system awaits the next P-wave. If there is a safety time out while awaiting the next P-wave, the system awaits the next R-wave and delivers the shock in synchrony with the ventricular R-wave. If a P-wave is sensed, the system starts the atrial absolute refractory timer (ABSREF) during which time a shock can be delivered. If an R-wave is sensed during the atrial absolute refractory time, then the shock is delivered. If the absolute refractory timer times out, the system is now entering the vulnerable zone in the atrium. Therefore, the system starts a relative refractory timer (RELREF) and awaits the time out of the relative refractory timer before proceeding. When the relative refractory timer has timed out, the system waits for the next R-wave, P-wave or a safety exit. If a safety exit occurs, then at the next R-wave the system delivers the shock. It is also safe to deliver the shock at the next sensed R-wave. However, if a P-wave is sensed, the system returns back to starting the absolute refractory timer.

A timing diagram illustrating the synchronizing of the ventricular shock with the atrial safe zone is set forth in FIG. 6. Referring to FIG. 6, the top line a is the atrium and has a sequence of P-waves. The atrial safety zone is shown on the second line b, and it can be seen that the absolute refractory timer begins on sensing the P-wave. It continues for a period during which if an R-wave had been sensed, a shock could be delivered. The Third line c shows the R-waves of the ventricle.

It can be seen that the relative refractory timer starts after the absolute refractory timer times out, and that is the vulnerable zone during which a shock cannot be delivered. When the vulnerable zone is over, the atrium is back in its safety zone and the safety zone continues until the next P-wave and the next absolute refractory timer times out. Thus if the system senses an R-wave simultaneously with the safe zone of the atrium, then it is safe to synchronize a shock as shown in the fourth line d. If the system were unable to synchronize the shock as shown in line d, when the safety timer (shown in the last line e) had timed out, the system would have synchronized the shock to the next ventricular event at that time.

It can be seen that the present invention concerns the use of a DDI mode pacer combined with a defibrillator. This enables this system to synchronize the shock with the atrium rather than with the ventricle, under certain circumstances. The synchrony with the atrium can be seen by referring to FIG. 5 where it is indicated that if fibrillation is detected, the system awaits the next P-wave and, if the arrhythmia is still in progress, the shock is delivered. Hence the R-wave is not used for synchrony in this case. Instead, ventricular therapy is delivered in synchrony with the atrium.

In the illustrative embodiment, the absolute refractory timer is approximately 80 msecs. Thus when the next P-wave is sensed, the shock must be delivered within the next 80 msecs. or else the system will be locked out during the relative refractory period of about 150 msecs.

In summary, it is seen that the pacing system of the invention operates to always inhibit if there is a spontaneous event in either chamber. If there is an absence of the event in the ventricle, a pacing pulse is always delivered. However, if there is an absence of an event in the atrium, the atrium may or may not be paced. If a ventricular event proceeded the atrial event by the V-A delay or greater than the V-A delay, the atrium is paced. However, if the ventricular event proceeded the atrial event by less than the V-A delay, the system does not pace and checks for arrhythmia, and then goes into tachycardia or fibrillation therapy.

As a result of the foregoing, dual chamber bradycardia support is provided to defibrillator patients and the incidence of atrial fibrillation caused by ventricular defibrillation shocks is reduced.

Although an illustrative embodiment of the invention has been shown and described, it is to be understood that various modifications and substitutions may be made by those skilled in the art without departing from the novel spirit and scope of the present invention.

What is claimed is:

1. A method for treating cardiac arrhythmia with an implanted pulse generator having sensing leads adapted to be connected to the atrium and the ventricle, which comprises the steps of:
   sensing the ventricle to determine if a ventricular arrhythmia is present;
   sensing the atrium to determine if an atrial arrhythmia is present;
   if the sensed atrial arrhythmia is determined to be more severe than the sensed ventricular arrhythmia, then not treating for a ventricular arrhythmia; but
   if the sensed atrial arrhythmia is determined to be less severe than the ventricular arrhythmia, then treating for a ventricular arrhythmia.

2. A method for treating cardiac arrhythmia with an implanted pulse generator having sensing leads adapted to be connected to the atrium and the ventricle, which comprises the steps of:
   sensing the ventricular rate to determine if a ventricular arrhythmia is present;
   sensing the atrial rate;
   if the sensed ventricular rate is greater than a selected tachycardia rate but less than a selected fibrillation rate, then determining whether the sensed atrial rate is greater than a selected fibrillation rate;
   if the sensed atrial rate is determined to be greater than a selected fibrillation rate, then not treating for a ventricular arrhythmia; but
   if the sensed atrial rate is determined to be not greater than a selected fibrillation rate, than treating for a ventricular arrhythmia.

3. A method as described in claim 2, including the step of determining whether the sensed ventricular rate is greater than a selected treatment-required rate; and if the selected ventricular rate is determined to be grater than the selected treatment-required rate, then treating for a ventricular arrhythmia.

4. A method as described in claim 3, wherein if the sensed ventricular rate is not greater than the selected fibrillation rate, then determining if the ventricular rate is greater than the selected tachycardia rate.

5. A method for treating cardiac arrhythmia with an implanted pulse generator having sensing means, energy storage means, and a sensing lead having a proximal end and a distal end, said proximal end connected to said sensing means and said distal end adapted to be connected to a heart, which comprises the steps of:
   providing a first voltage supply to said sensing means;
   providing a second, different voltage supply to said energy storage means;
   sensing the heart to determine if an arrhythmia is present;
   if an arrhythmia is present, then commencing the charging of said energy storage means via said second voltage supply and continuing to sense the heart; and
   if the arrhythmia ceases, then discontinuing said charging.

6. A method as described in claim 5, including the step of determining whether then energy storage means is charged to a predetermined level; and if the energy storage means is charged to said predetermined level and the arrhythmia is still present, then delivering a shock to the heart during a time period that is outside the vulnerable zones of the atrium and the ventricle.

7. A method as described in claim 6, in which the shock is not delivered during a predetermined time zone after sensing a P-wave.

8. A method as described in claim 5, in which a shock is delivered to the heart, if the arrhythmia is still present, during a time period that is outside the vulnerable zones of the atrium and the ventricle.

9. A method as described in claim 8, in which the shock is delivered in synchrony with an atrial event.

10. A method as described in claim 5, wherein if the arrhythmia continues, then determining whether the ventricular rate is greater than a selected fibrillation rate; and if the ventricular rate is greater than said selected fibrillation rate, then delivering a shock during a predetermined time zone after sensing a P-wave.

11. A method as described in claim 10, wherein if the ventricular rate is not greater than a selected fibrillation rate but is greater than a selected tachycardia rate, then delivering a shock to the heart in synchrony with an R-wave outside of the vulnerable zones of the atrium and the ventricle.

12. A method as described in claim 10, wherein if the ventricular rate is not greater than a selected fibrillation rate but is greater than a selected tachycardia rate, then providing a safety timing period before delivering any shock to the heart.

13. A method for treating cardiac arrhythmia with an implanted pulse generator having sensing leads adapted to be connected to the atrium and the ventricle, which comprises the steps of:
sensing the ventricle to determine if an arrhythmia is present;
if an arrhythmia is present, then commencing the charging of energy storage means;
if the arrhythmia ceases, then discontinuing said charging;
if the arrhythmia does not cease, determining whether the energy storage means is charged;
if the energy storage means is charged and the arrhythmia is still present, then determining whether the ventricular rate is greater than a selected treatment-required rate;
if the ventricular rate is greater than said selected treatment-required rate, then delivering a shock to the heart a predetermined time after sensing a P-wave and during a time period that is outside the vulnerable zones of the atrium and the ventricle.

14. A method as described in claim 13, wherein:
if the ventricular rate is not greater than a selected treatment-required rate but is greater than a selected tachycardia rate, then delivering a shock to the heart in synchrony with an R-wave outside of the vulnerable zones of the atrium and the ventricle; and
if the ventricular rate is not greater than a selected treatment-required rate but is greater than a selected tachycardia rate, then providing a safety timing period before delivering any shock to the heart.

15. A method for combined cardiac pacing and defibrillating comprising the steps of:
implanting a DDI pacer/defibrillator having a V—V timer and a V-A timer;
connecting sensing and pacing leads to the atrium and the ventricle:
sensing for P-waves;
sensing for R-waves;
resetting the V—V timer and the V-A timer if an R-wave is sensed;
providing a pacing stimulus to the ventricle if no R-wave is sensed during the V—V time interval;
inhibiting the pacing stimulus to the ventricle if an R-wave is sensed during the V—V interval;
inhibiting a pacing stimulus to the atrium if a P-wave is sensed during the V-A time interval;
if an R-wave is sensed during the V—V time interval, then determining if an arrhythmia is present;
if an arrhythmia is present, then commencing the charging of energy storage means; and if the arrhythmia ceases, then discontinuing said charging.

16. A method for combined cardiac pacing and defibrillating with an implanted pacer/defibrillator having a first timer having a first time interval, a second timer having a second time interval, and sensing and pacing leads adapted to be connected to the atrium and the ventricle, which comprises the steps of:
(a) sensing for P-waves;
(b) sensing for R-waves;
(c) resetting the first and second timers if an R-wave is sensed;
(d) providing a pacing stimulus to the ventricle if no R-wave is sensed during the first time interval;
(e inhibiting the pacing stimulus to the ventricle if an R-wave is sensed during the first time interval;
(f) inhibiting a pacing stimulus to the atrium if a P-wave is sensed during the second time interval;
(g) if an R-wave is sensed during the first time interval, then determining the presence of an arrhythmia;
(h) providing arrhythmia therapy if an arrhythmia is determined to be present;
(i) the step of determining the presence of an arrhythmia comprising the step of determining whether the sensed ventricular rate is greater than a selected fibrillation rate;
(j) if the sensed ventricular rate is greater than said selected fibrillation rate, then providing arrhythmia therapy; and
(k) if the sensed ventricular rate is greater than a selected tachycardia rate but less than a selected fibrillation rate, then determining whether the sensed atrial rate is greater than a selected atrial fibrillation rate, and if the sensed atrial rate is greater than a selected atrial fibrillation rate, then not delivering arrhythmia therapy.

17. A method for combined cardiac pacing and defibrillating with an implanted pacer/defibrillator having a first timer having a first time interval, a second timer having a second time interval, and sensing and pacing leads adapted to be connected to the atrium and the ventricle, which comprises the steps of:
(a) sensing for P-waves;
(b) sensing for R-waves;
(c) resetting the first and second timers if an R-wave is sensed;
(d) providing a pacing stimulus to the ventricle if no R-wave is sensed during the first time interval;
(e) inhibiting the pacing stimulus to the ventricle if an R-wave is sensed during the first time interval;
(f) inhibiting a pacing stimulus to the atrium if a P-wave is sensed during the second time interval;
(g) if an R-wave is sensed during the first time interval, then determining the presence of an arrhythmia;

(h) providing arrhythmia therapy if an arrhythmia is determined to be present;

(i) the step of determining the presence of an arrhythmia comprising the step of determining whether the sensed ventricular rate is greater than a selected fibrillation rate;

(j) if the sensed ventricular rate is greater than said selected fibrillation rate, then providing arrhythmia therapy; and (k) if the sensed ventricular rate is greater than a sensed tachycardia rate but less than a selected fibrillation rate, then determining whether the sensed atrial fibrillation rate is greater than a selected atrial fibrillation rate, and if the sensed atrial rate is not greater than the selected fibrillation rate, then providing arrhythmia therapy.

18. A method for combined cardiac passing and defibrillating with an implanted DDI pacer/defibrillator having a first timer having a first timing interval, a second timer having a second timing interval, and sensing and pacing leads adapted to be connected to the atrium and the ventricle, which comprises the steps of:

sensing for P-waves;

sensing for R-waves;

resetting the first and second timers if an R-wave is sensed;

providing a pacing stimulus to the ventricle if no R-wave is sensed during the first time interval;

inhibiting the pacing stimulus to the ventricle if an R-wave is sensed during the first time interval;

inhibiting a pacing stimulus to the atrium if a P-wave is sensed during the second time interval;

if an R-wave is sensed during the first time interval, then determining the presence of an arrhythmia;

if no arrhythmia is determined to be present, then resetting said first and second timers;

if no R-wave or P-wave is sensed during the second time interval, then providing a pacing stimulus to the atrium only if an R-wave was sensed during the previous first time intervals;

the step of determining the presence of an arrhythmia comprising the step of determining whether the sensed ventricular rate is greater than a selected fibrillation rate;

if the sensed ventricular rate is greater than said selected fibrillation rate, then providing arrhythmia therapy;

if the sensed ventricular rate is greater than a selected tachycardia rate but less than a selected fibrillation rate, then determining whether the sensed atrial rate is greater than a selected fibrillation rate; and if the sensed atrial rate is greater than a selected fibrillation rate, then resetting said first and second timers but if the sensed atrial rate is not greater than a selected fibrillation rate, then providing arrhythmia therapy.

19. A method for combined cardiac pacing and defibrillating with an implanted pacer/defibrillator having a first timer having a first timing interval, a second timer having a second timing interval, and sensing and pacing leads adapted to be connected to the atrium and the ventricle, which comprises the steps of:

sensing for Pwaves;

sensing for R-waves; resetting the first and second timers if an R-wave is sensed;

providing a pacing stimulus to the ventricle if no R-wave is sensed during the first time interval;

inhibiting the pacing stimulus to the ventricle if an R-wave is sensed during the first time interval;

inhibiting a pacing stimulus to the atrium if a P-wave is sensed during the second time interval;

if an R-wave is sensed during the first time interval, then determining if an arrhythmia is present;

if an arrhythmia is present, then commencing the charging of energy storage means;

if the arrhythmia ceases, then discontinuing said charging;

if the sensed ventricular rate is greater than a selected tachycardia rate but less than a selected fibrillation rate, then determining whether the sensed atrial rate is greater than a selected fibrillation rate;

if the sensed atrial rate is determined to be greater than a selected fibrillation rate, then not treating for an arrhythmia; but if the sensed atrial rate is not greater than a selected fibrillation rate, then treating for an arrhythmia.

20. A method as described in claim 19, wherein if the ventricular rate is not greater than a selected fibrillation rate but is greater than a selected tachycardia rate, than providing a safety timing period before delivering any shock to the heart.

21. A method for combined cardiac pacing and defibrillating with an implanted pacer/defibrillator having a first timer having a first timing interval, a second timer having a second timing interval, and sensing and pacing leads adapted to be connected to the atrium and the ventricle, which comprises the steps of:

sensing for P-waves;

sensing for R-waves;

resetting the first and second timers if an R-wave is sensed;

providing a pacing stimulus to the ventricle if no R-wave is sensed during the first time interval;

inhibiting the pacing stimulus to the ventricle if an R-wave is sensed during the first time interval;

inhibiting a pacing stimulus to the atrium if a P-wave is sensed during the second time interval;

if an R-wave is sensed during the first time interval, then determining if an arrhythmia is present;

if an arrhythmia is present, then commencing the charging of energy storage means;

if the arrhythmia ceases, then discontinuing said charging;

determining if an atrial arrhythmia is present; determining if a ventricular arrhythmia is present;

if the atrial arrhythmia is more severe than the ventricular arrhythmia, then not treating for an arrhythmia;

but if the ventricular arrhythmia is more sever than the atrial arrhythmia, then treating for an arrhythmia.

22. An implantable pulse generator for treating cardiac arrhythmia, which comprises:

a sensing lead for connection to a chamber of the heart, said sensing lead having a distal end for connection to the heart and a proximal end;

sensing circuit means for connection to said proximal end;

energy storage means;

means for providing a first voltage supply to said sensing circuit means;

means for providing a second, different voltage supply to said energy storage means;

means for sensing the heart chamber to determine if an arrhythmia is present;

means for commencing the charging of said energy storage means via said second voltage supply if an arrhythmia is present, and for discontinuing said charging if the arrhythmia ceases, with said sensing circuit means being operable to continue sensing the heart chamber during said charging.

23. An implantable pulse generator as defined by claim 22, in which said first and second voltage supplies are derived from a common battery energy source.

* * * * *